(12) United States Patent
Kim et al.

(10) Patent No.: US 8,741,927 B2
(45) Date of Patent: Jun. 3, 2014

(54) PRODUCTION METHOD OF INTERMEDIATE COMPOUND FOR SYNTHESIZING MEDICAMENT

(75) Inventors: Bong Chan Kim, Daejeon (KR); Kyu Young Kim, Daejeon (KR); Hee Bong Lee, Daejeon (KR); Ji Eun An, Daejeon (KR); Kyu Woong Lee, Daejeon (KR)

(73) Assignee: LG Life Sciences Ltd., Seoul (KR)

(*) Notice: Subject to any disclaimer, the term of this patent is extended or adjusted under 35 U.S.C. 154(b) by 0 days.

(21) Appl. No.: 13/820,197

(22) PCT Filed: Aug. 25, 2011

(86) PCT No.: PCT/KR2011/006260
§ 371 (c)(1),
(2), (4) Date: Mar. 1, 2013

(87) PCT Pub. No.: WO2012/030106
PCT Pub. Date: Mar. 8, 2012

(65) Prior Publication Data
US 2013/0165659 A1   Jun. 27, 2013

(30) Foreign Application Priority Data
Sep. 3, 2010 (KR) .................. 10-2010-0086619

(51) Int. Cl.
*A01N 43/40* (2006.01)
*A61K 31/445* (2006.01)
*A61K 31/435* (2006.01)
*A61K 31/44* (2006.01)
*C07D 211/00* (2006.01)
*C07D 211/72* (2006.01)
*C07D 211/84* (2006.01)
*C07D 213/63* (2006.01)
*C07D 213/70* (2006.01)

(52) U.S. Cl.
USPC ........... 514/315; 514/277; 514/345; 514/357; 546/243; 546/290; 546/314

(58) Field of Classification Search
USPC ........................................ 514/315
See application file for complete search history.

(56) References Cited

U.S. PATENT DOCUMENTS

| | | | | |
|---|---|---|---|---|
| 4,456,768 A * | 6/1984 | Fried | ............... | 562/503 |
| 4,851,344 A | 7/1989 | Simon et al. | | |
| 5,556,982 A | 9/1996 | Fritzberg et al. | | |
| 2002/0013341 A1 * | 1/2002 | Duan et al. | ............... | 514/312 |
| 2008/0039517 A1 | 2/2008 | Washburn et al. | | |

FOREIGN PATENT DOCUMENTS

| | | |
|---|---|---|
| EP | 0 279 435 A2 | 8/1988 |
| WO | WO 2006/104356 A1 | 10/2006 |

OTHER PUBLICATIONS

Tornoe; J. Org. Chem. 2002, 67, 3057-3064.*
Wuts ; Greene's Protective Groups in Organic Synthesis, Fourth Edition, 2007 John Wiley & Sons, Inc., pp. 986-1051.*
Smith "March's Advanced Organic Chemistry—Reactions, Mechanisms, and Structure" 6th Ed, 2007, John Wiley & Sons, chapter 10, pp. 496-502.*
Kawai; Bioorg. Med. Chem. Lett., 2007, 17, 5537-5542.*
Mangette; Tetrahedron, 2009, 65, 9536-9541.*
Montalbetti; Tetrahedron, 2005, 61, 10827-10852.*
Seo; Bioorganic & Medicinal Chemistry, 2007, 15, 1928-1938.*
Hayashi et al., "First asymmetric total synthesis of synerazol, an antifungal antibiotic, and determination of its absolute stereochemistry," The Journal of Organic Chemistry, vol. 70, 2005, pp. 5643-5654.
Maetz et al., "A Simple Preparation of N-Protected Chiral α-Aminonitriles from N-Protected α-Amino Acid Amides," Tetrahedron Letters, vol. 38, No. 24, 1997, pp. 4221-4222,.
Pozdnev, "Activation of carboxylic acids by pyrocarbonates. Application of di-tert-butyl pyrocarbonate as condensing reagent in the synthesis of amides of protected amino acids and peptides," Tetrahedron Letters, vol. 36, No. 39, 1995, pp. 7115-7118.
Seki et al., "A Facile Synthesis of (S)-4-Hydroxypyrrolidin-2-one from (S)-Malic Acid," Short Paper, Synthesis, No. 5, 1999, pp. 745-747.
Collins et al., "Facile Reduction of Tertiary Lactams to Cyclic Amines With 9-Borabicyclo[3.3.1]nonane (9-BBN)," Tetrahedron Letters, vol. 40, 1999, pp. 3673-3676.
Flaniken et al., "Aminoborohydrides. 11. Facile Reduction of N-Alkyl Lactams to the Corresponding Amines Using Lithium Aminoborohydrides," Organic Letters, vol. 1, No. 5, 1999, pp. 799-801.
Igarashi et al., "Transition-metal complex-catalyzed reduction of amides with hydrosilanes: a facile transformation of amides to amines," Tetrahedron Letters, vol. 42, 2001, pp. 1945-1947.
Kuwano et al., "Reduction of Amides to Amines via Catalytic Hydrosilylation by a Rhodium Complex," Tetrahedron Letters, vol. 39, 1998, pp. 1017-1020.
Li et al., "The 5-substituted piperazine as a novel secondary pharmacophore greatly improving the physical properties of urea-based inhibitors of soluble epoxide hydrolase," Bioorganic & Medicinal Chemistry, vol. 14, 2006, pp. 6586-6592.
Malkov et al., "Asymmetric Allylic Substitution Catalyzed by C1-Symmetrical Complexes of Molybdenum: Structural Requirements of the Ligand and the Stereochemical Course of the Reaction," Chemistry A European Journal, vol. 12, 2006, pp. 6910-6929.
Treder et al., "A New Approach to the Synthesis of Selectively Protected (2S)-1,2,4-Triaminobutane Derivatives," Synthesis 2005, No. 14, pp. 2281-2283.
International Search Report, issued in PCT/KR2011/006260, mailed Mar. 26, 2012.
López-García et al., "Synthesis of (R)—3, 4—Diaminobutanoic Acid by Desymmetrization of Dimethyl 3-(Benzylamino) glutarate through Enzymatic Ammonolysis", Journal of Organic Chemistry, 2003, vol. 68, No. 2, pp. 648-651.
Washburn et al., "Discovery of orally active, pyrrolidinone-based progesterone receptor partial agonists", Bioorganic & Medicinal Chemistry Letters, 2009, vol. 19, No. 16, pp. 4664-4668.

* cited by examiner

*Primary Examiner* — John Mabry
*Assistant Examiner* — Daniel Carcanague
(74) *Attorney, Agent, or Firm* — Birch, Stewart, Kolasch & Birch, LLP

(57) ABSTRACT

The present invention relates to a novel method for preparing a compound of formula (2) as the intermediate, which can be effectively used for preparation of a compound of formula (1) exhibiting good inhibitory activity against dipeptidyl peptidase IV enzyme.

22 Claims, No Drawings

PRODUCTION METHOD OF INTERMEDIATE COMPOUND FOR SYNTHESIZING MEDICAMENT

TECHNICAL FIELD

The present invention relates to a novel method for production of a compound of formula (2) as the major intermediate for synthesizing a compound of formula (1), which exhibits good inhibitory activity for Dipeptidyl Peptidase-IV (DPP-IV) and thus can be used as a medicinal product.

BACKGROUND ART

The compound of formula (1), as the compound which has been disclosed in International Patent Publication WO 06/104356, exhibits a good inhibitory activity for Dipeptidyl Peptidase-IV enzyme, and therefore can be effectively used for treatment and prevention of diseases caused by the action of Dipeptidyl Peptidase-IV, including diabetes (particularly, type II diabetes), obesity, etc.

The methods for preparing the compound of formula (1) by means of the compound of formula (2) as the intermediate have been disclosed in WO 06/104356. Regarding said prior reference, the compounds of formulas (1) and (2) can be prepared by methods—for example, such as the following reaction scheme 1:

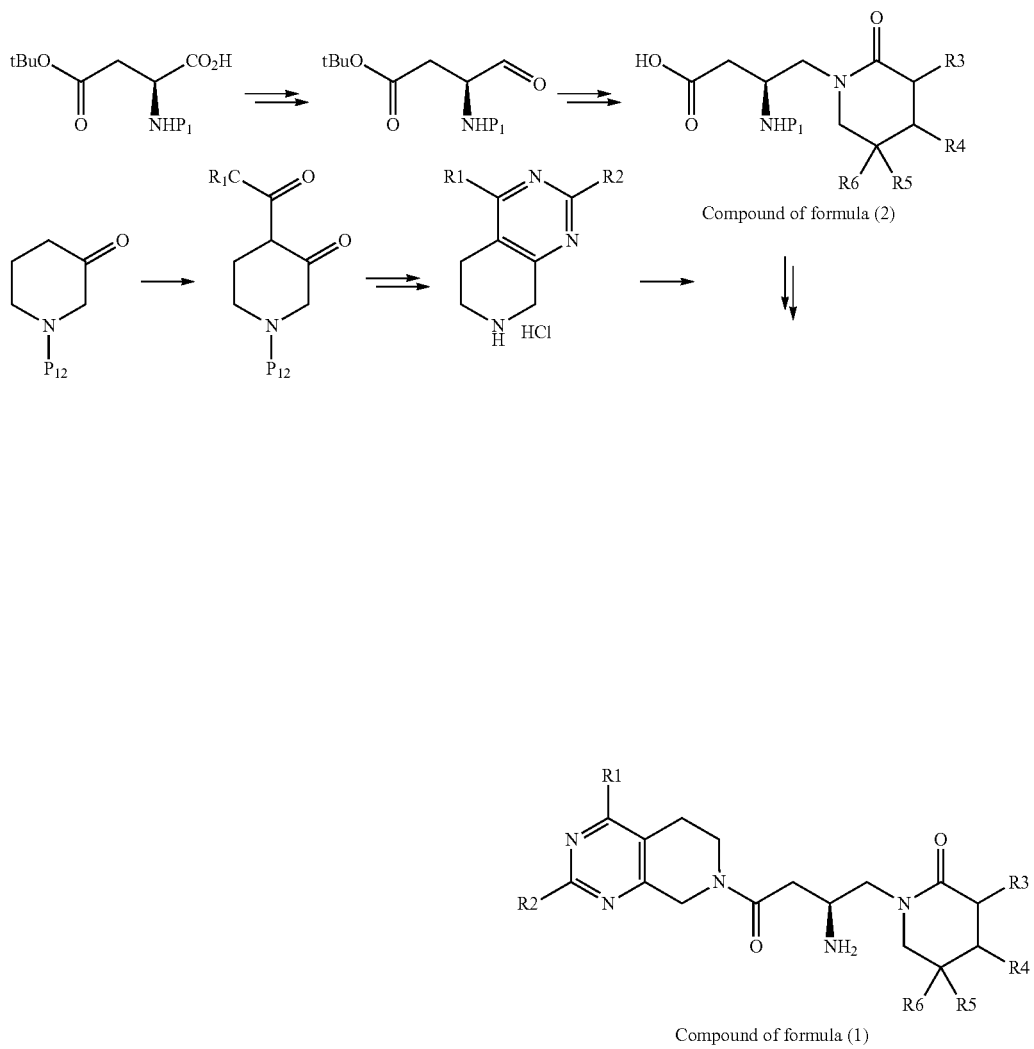

However, in mass-scale production said prior method is difficult to obtain the compound of formula (2) having a high optical purity due to the racemization of a stereogenic center on which the amine group is present in the compound of formula (2) to some extent, and therefore it is also difficult to obtain the compound of formula (1) with a high optical purity.

DISCLOSURE OF INVENTION

Technical Problem

The object of the present invention is to provide a novel method for preparing the compound of formula (2), with high optical purity, as the major intermediate for preparing the compound of formula (1), which can be medically used as an agent for inhibiting DPP-IV.

Solution to Problem

Therefore, the present invention provides a novel method for preparing the compound of formula (2) as the major intermediate, which can be effectively used for preparation of the compound of formula (1) as an agent for inhibiting DPP-IV:

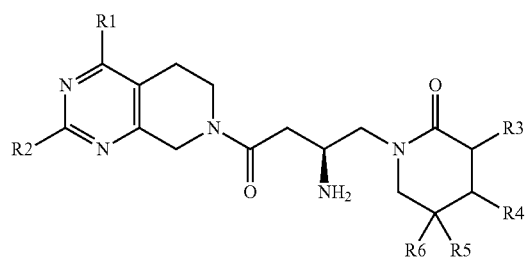

(1)

In the above formula,

R1 is hydrogen or $CF_3$,

R2 is selected from the group consisting of hydrogen, substituted or unsubstituted $C_1$-$C_{10}$ alkyl, substituted or unsubstituted $C_3$-$C_{10}$ cycloalkyl, substituted or unsubstituted $C_4$-$C_8$ aryl, and substituted or unsubstituted $C_3$-$C_7$ heteroaryl; and each of R3, R4, R5 and R6 is independently hydrogen, halogen, or substituted or un-substituted $C_1$-$C_4$ alkyl.

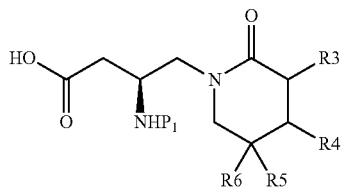

(2)

In the above formula, R3, R4, R5 and R6 are as defined above, and $P_1$ is an amine-protecting group. Preferably, $P_1$ is Boc (butyloxycarbonyl), Cbz (benzyloxycarbonyl) or Fmoc (9-fluorenylmethyloxycarbonyl) and more preferably, Boc.

In the above formulas (1) and (2), if $C_1$-$C_4$ alkyl is substituted, it can be preferably substituted with halogen, and more preferably, fluorine.

1. Preparation of the Compound of Formula (2)

The method for preparation of the compound of formula (2) according to the present invention is characterized in that a compound of formula (4) is reacted with a compound of formula (5) and further comprises the step of removing a carboxylic acid protecting group derived from the compound of formula (4) after the reaction of said two compounds.

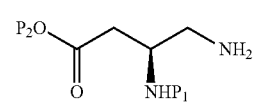

(4)

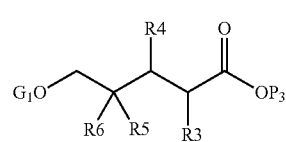

(5)

In the above formulas, $P_1$, R3, R4, R5 and R6 are as defined above;

each of $P_2$ and $P_3$ is independently benzyl group, methyl group, ethyl group, i-propyl group or t-butyl group;

$G_1$ functions as a good leaving group together with oxygen. $G_1O$ is triflate (trifluoromethanesulfonate), mesylate, tosylate, besylate or nonaflate (nonafluorobutanesulfonate) and preferably triflate or nonaflate.

The method of the present invention produces the compound of formula (2) from the compound of formula (4) and the compound of formula (5) via a compound of formula (2a), and specifically comprises:

(a) the step of coupling reaction by addition of a base to the compound of formula (4) and the compound of formula (5), (b) the step of cyclization by addition of an acid to obtain the compound of formula (2a), and (c) the step of removing the carboxylic acid protecting group by hydrolysis of the resulting compound of formula (2a) to obtain the compound of formula (2).

The method of the present invention can be represented as the following reaction schemes 2 and 3.

Reaction Scheme 2

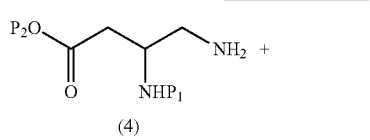

(4)

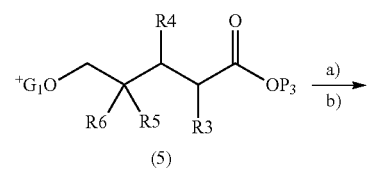

(5)

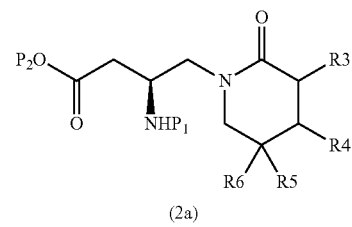

(2a)

Reaction Scheme 3

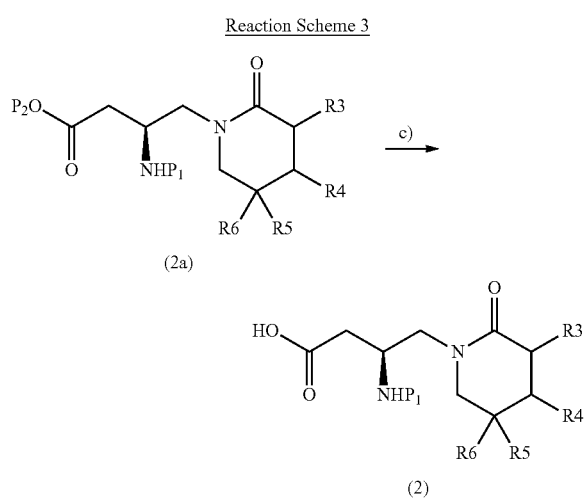

In the above schemes, a is a base such as Et$_3$N, Hunig's base, etc.;

is an acid such as AcOH, etc., and an organic solvent such as CH$_2$Cl$_2$, etc.;

c varies with the protecting group and typically is selected from the conditions (1) a strong acid such as H$_2$SO$_4$, etc. and CH$_2$Cl$_2$, aq. NaOH, Boc$_2$O, and (2) NaOH, EtOH, H$_2$O, reflux, when P$_1$ is Boc and P$_2$ is t-butyl group or is the hydrolysis condition utilizing the base specified in the above condition (2), when P$_1$ is Boc and P$_2$ is benzyl group, methyl group, ethyl group and i-propyl group. R3, R4, R5, R6, P$_1$, P$_2$, P$_3$ and G$_1$ are as defined above.

Specifically, in step (a) the unprotected primary amine of the compound of formula (4) is coupled with a carbon atom having the leaving group in the compound of formula (5) under the basic condition, and —OG$_1$ is removed. This reaction uses C$_1$-C$_4$ trialkylamine, preferably triethylamine or diisopropylethylamine, as the base. As the reaction solvent, common organic solvents such as dichloroethane or dichloromethane, or cyclic ethers (e.g., tetrahydrofuran (THF) or dioxane) can be used. To facilitate the reaction, the base used alternatively serves as the solvent. The reaction can be conducted at any temperature between 0° C. and the refluxing temperature.

In step (b), the compound of formula (2a) is synthesized through cyclization of the secondary amine group of the compound produced from said step (a), with the internal ester group under the acidic condition. In this reaction, as the acid inorganic acids such as hydrochloric acid, sulfuric acid, nitric acid, phosphoric acid, etc. or organic acids such as formic acid, acetic acid, tartaric acid, etc. can be used, with acetic acid being particularly preferable. The solvent and temperature conditions as described in the above step (a) can be used in this step. Said steps (a) and (b) are conducted in a continuous manner.

In step (c), the compound of formula (2a) obtained from step (b) is hydrolyzed to obtain the compound of formula (2). Specifically, in case of the compound of formula (2a) where P$_1$ is Boc and P$_2$ is t-butyl group, first a strong acid such as sulfuric acid, hydrochloric acid, phosphoric acid, TFA (trifluoroacetic acid), etc. can be used to remove both protecting groups and Boc protecting group can then be attached again to the amine group under the basic condition to obtain the desired compound of formula (2). Alternatively, the hydrolysis under the basic condition, rather than the acidic condition, can lead to selective removal of only P$_2$ among the protecting groups P$_1$ and P$_2$ to provide the compound of formula (2), and this manner of the procedure is more efficient. Preferably, sodium hydroxide solution is used as the base. Upon completion of the reaction, the compound of formula (2) can be obtained as a solid product through acidification using an acid.

In case of the compound where P$_1$ is Boc and P$_2$ is benzyl group, methyl group, ethyl group or i-propyl group, the hydrolysis can be conducted by means of a base. The deprotecting reaction is conducted using H$_2$/Pd—C when P$_1$ is Cbz, or using Bu$_4$N$^+$F$^-$ when P$_1$ is Fmoc.

Preferably, the compound of formula (2) can be obtained in a high yield when P$_2$ is t-butyl group or i-propyl group, more preferably t-butyl group, and P$_3$ is methyl group or ethyl group.

In addition, the present invention provides a method for preparation of the compounds of formulas (4) and (5) as the starting materials used for preparation of the compound of formula (2).

2. Preparation of the Compound of Formula (5)

The compound of formula (5), as one of the starting materials used for preparation of the compound of formula (2), can be prepared from the known compound of formula (7), which can be obtained from a compound of formula (6) through the method shown in the following reaction scheme 4, as disclosed in WO 06/104356.

The method for preparation of the compound of formula (5) comprises (a) the step of reducing the compound of formula (7) to obtain a primary alcohol compound; and (b) the step of reacting the alcohol compound obtained from the above with a G1 compound corresponding to the portion G$_1$O of the compound of formula (2) to obtain the compound of formula (5). This method can be represented as shown in the following reaction scheme 5.

Reaction Scheme 4

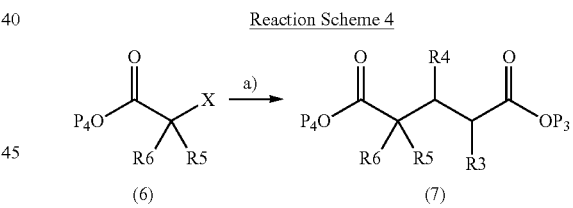

In the above scheme, a is ethyl acrylate (where P$_4$ is ethyl), Cu powder, TMEDA (tetramethylethylenediamine) or THF;

X is a halogen such as Br, F or Cl, etc.;

P$_4$ is benzyl group, methyl group, ethyl group, i-propyl group or t-butyl group;

R3, R4, R5, R6 and P$_3$ are as defined above.

Reaction Scheme 5

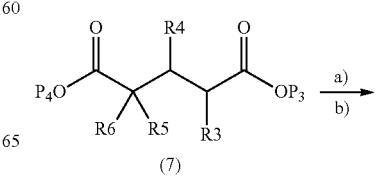

-continued

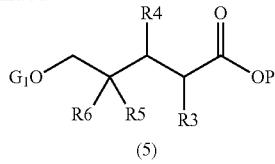

(5)

In the above scheme, a is $NaBH_4$, and EtOH or MeOH or i-PrOH;

b is trifluoromethane sulfonic acid anhydride ($Tf_2O$), trifluoromethane sulfonyl chloride (TfCl), methanesulfonyl chloride (MsCl), toluenesulfonyl chloride (TsCl), bromobenzenesulfonyl chloride (BsCl), $(CF_3(CF_2)_3SO_2)F$ or $(CF_3(CF_2)_3SO_2)_2O$, pyridine or trialkylamine, and $CH_2Cl_2$;

R3, R4, R5, R6, $P_3$, $P_4$ and $G_1$ are as defined above.

Specifically, in the above step (a) sodium borohydride ($NaBH_4$) is used to selectively reduce only the ester group, $P_4$, protecting the carboxylic acid to obtain the primary alcohol compound, which in step (b) is then reacted with the $G_1$ compound corresponding to the portion $G_1O$ of the compound of formula (2)—i.e., $G_1$ compound selected from the group consisting of trifluoromethane sulfonic acid anhydride ($Tf_2O$), trifluoromethane sulfonyl chloride (TfCl), methanesulfonyl chloride (MsCl), toluenesulfonyl chloride (TsCl), bromobenzenesulfonyl chloride (BsCl), $(CF_3(CF_2)_3SO_2)F$ and $(CF_3(CF_2)_3SO_2)_2O$, in $CH_2Cl_2$ as the solvent in the presence of pyridine or trialkylamine to obtain the compound of formula (5). By way of example, when $G_1O$ of the desired compound of formula (2) is triflate, the reaction is conducted using trifluoromethane sulfonic acid anhydride to obtain the compound of formula (5).

3. Preparation of the Compound of Formula (4)

Meanwhile, the compound of formula (4) as the remaining one of the starting materials for preparing the compound of formula (2) can be prepared according to any one of the following methods.

The first method for preparing the compound of formula (4) comprises (a) the step of converting a carboxylic acid group of a compound of formula (8) into an ester group by introducing $P_2$ group to obtain a compound of formula (9), (b) the step of selectively reducing an ester group $P_5$ present in the compound of formula (9) to obtain a compound of formula (10), (c) the step of introducing a $G_2O$ leaving group into the compound of formula (10) to obtain a compound of formula (11), (d) the step of reacting the compound of formula (11) with an azide compound to obtain a compound of formula (12) and (e) the step of subjecting the compound of formula (12) to hydrogenation to obtain the compound of formula (4).

The first method for preparing the compound of formula (4) as described above comprises the procedures for introducing the amine group into the carbon atom to which the ester group is attached in the compound of formula (8) and can be represented as shown in the following reaction scheme 6.

Reaction Scheme 6

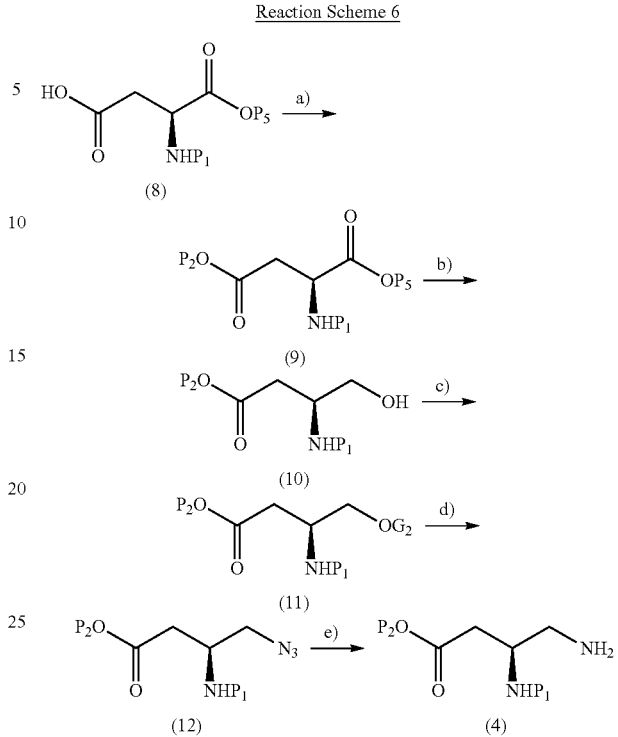

In the above scheme, a is DMAP, $Boc_2O$ (where $P_2$ is t-butyl group), and t-BuOH or THF;

b is $NaBH_4$, and MeOH or EtOH;

c is $Tf_2O$, MsCl, TsCl, $(CF_3(CF_2)_3SO_2)F$ or $(CF_3(CF_2)_3SO_2)_2O$ etc., pyridine or trialkylamine, $CH_2Cl_2$;

d is $NaN_3$, DMF or NMP or DMAc or DMAc/EtOAc or DMAc/$H_2O$ or DMAc/MeOH, heating;

e is selected from the conditions (1) $H_2$, Pd/C, MeOH or EtOH, (2) $NaBH_4$, Pd/C, MeOH, (3) $PPh_3$, $H_2O$, THF, and (4) trialkyl phosphine or trialkylphosphite, $H_2O$, THF;

$P_5$ is methyl group, ethyl group, i-propyl group or t-butyl group;

$G_2$ is together with oxygen a good leaving group including triflate, mesylate, tosylate, besylate, nonaflate, etc.;

$P_1$ and $P_2$ are as defined above.

In step (a) of said reaction, the carboxylic acid group of formula (8) is converted into the ester group by introducing $P_2$ to produce the compound of formula (9). In this reaction, t-BuOH or THF is used as the solvent, and a catalytic amount (0.5 mol %-30 mol %) of 4-di(methylamino)pyridine (DMAP) is used. For example, if $P_2$ is introduced, when $P_2$ is t-butyl group, an equivalent of $Boc_2O$ is used, and the reaction is conducted in the range between room temperature and about 40° C. to obtain the desired ester compound of formula (9).

In step (b) of said reaction, the ester group which is originally present in the compound of formula (9)—i.e., the ester group present in the position of $P_5$—is selectively reduced with sodium borohyride ($NaBH_4$) to obtain the compound of formula (10) as the primary alcohol. In this reaction, methanol or ethanol is used as the solvent.

In step (c) of said reaction, the leaving group $G_2O$ is introduced through reaction with trifluoromethane sulfonic acid anhydride ($Tf_2O$), trifluoromethane sulfonyl chloride (TfCl), methanesulfonyl chloride (MsCl), toluenesulfonyl chloride (TsCl), bromobenzenesulfonyl chloride (BsCl), (CF$_3$(CF$_2$)$_3$SO$_2$)F or (CF$_3$(CF$_2$)$_3$SO$_2$)$_2$O, in CH$_2$Cl$_2$ as the solvent in the presence of pyridine or trialkylamine to obtain the compound of formula (11).

In step (d) of said reaction, the compound of formula (11) is reacted with 1.0 to 2.0 equivalents of sodium azide under warming condition (60° C. to 80° C.) to obtain the compound of formula (12).

The azide group of the compound of formula (12) thus obtained can be converted into the amine group through hydrogenation reaction under various reaction conditions (e) to obtain the compound of formula (4).

Particularly, when P$_1$ is Boc, P$_2$ is i-propyl group or t-butyl group and G$_2$O is triflate or nonaflate, the compound of formula (4) can be obtained in a high yield.

The second method for preparation of the compound of formula (4) comprises (a) the step of converting a carboxylic acid compound of formula (13) into an activated ester, which is then reacted with a secondary amine compound to obtain an amide compound of formula (14), (b) the step of reducing an amide group of the compound of formula (14) to obtain a tertiary amine compound of formula (15), and (c) the step of subjecting the tertiary amine compound of formula (15) to debenzylation reaction to obtain the compound of formula (4). This method can be represented as shown in the following reaction scheme 7.

Reaction Scheme 7

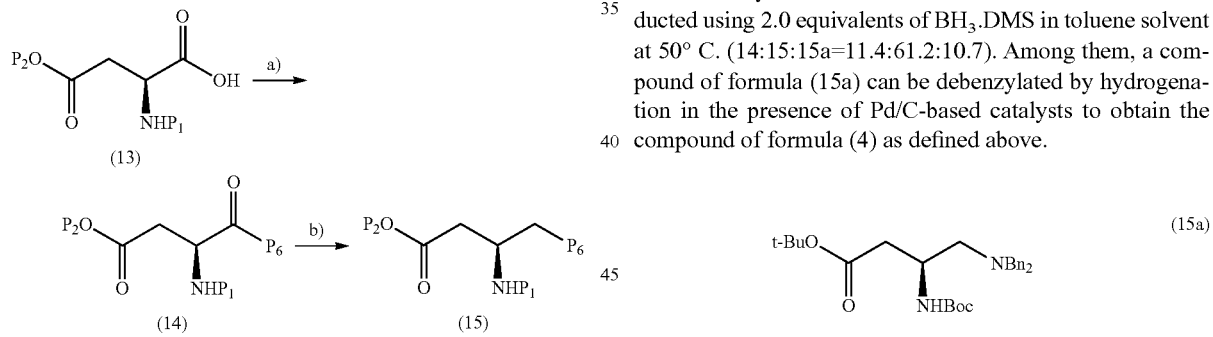

In the above scheme, a is selected from the conditions (1) i-BuOCOCl, NMM (N-methylmorpholine), Bn$_2$NH or BnNH$_2$ or diallylamine or allylamine; and (2) i-BuOCOCl, NMM, diallylamine;

b is selected from the conditions (1) Os(CO)$_{12}$, Ru(CO)$_{12}$, RuCl$_2$(CO)$_2$(PPh$_3$)$_2$ or RuH$_2$(CO)$_2$(PPh$_3$)$_2$ as the reaction catalyst, Et$_3$SiH, toluene, reflux, (2) RuH(CO)(PPh$_3$)$_3$, Ru$_3$(CO)$_{12}$ or RuCl(PPh$_3$)$_3$ as the reaction catalyst, Ph$_2$SiH$_2$, PMHS (polydimethylsiloxane), THF or 2-Me THF, 1,4-dioxane, ethyl ether, toluene, (3) 9-BBN (9-Borabicyclo[3,3,1]nonane), THF, reflux, and (4) BH$_3$.DMS or BH$_3$.THF, toluene, heating;

P$_6$ is monobenzylamine or dibenzylamine or monoallylamine or diallylamine,

P$_1$ and P$_2$ are as defined above.

In step (a) of said reaction, the amide compound of formula (14) can be conveniently obtained by converting the carboxylic acid compound of formula (13) into the activated ester with the action of isobutyl chloroformate and a base, and then reacting with a secondary amine such as Bn$_2$NH, diallylamine, etc.

In step (b) of said reaction, the amide group of the amide compound of formula (14) can be reduced through various methods known in the relevant technical field to obtain the tertiary amine compound of formula (15). For example, the methods for converting amide group into amine have been known as follows: Method b-1: see, for example, Tetrahydron Lett. 2001, 42, 1945; Method b-2: see, for example, Tetrahydron Lett. 1998, 39, 1017; Method b-3: see, for example, Org. Lett. 1999, 1, 799, and Tetrahydron Lett. 1999, 40, 3673; Method b-3: see, for example, Bioorg. Med. Chem. 2006, 14, 6586, and Chem. Eur. J. 2006, 12, 6910, and Synthesis 2005, 2281.

By way of example, in case of the compound of formula (14) where P$_1$ is Boc and P$_2$ is t-butyl, the desired compound of formula (15) can be obtained under various catalytic conditions of said b-1. In addition, the catalysts and conditions described in the above b-2 can be used to obtain the desired compound of formula (15). Particularly, when Ph$_2$SiH$_2$ is used under the catalyst Ru$_3$(CO)$_{12}$, the reaction can be conducted using 0.5 mol %~30 mol % of Ru$_3$(CO) and 5.0 equivalents of Ph$_2$SiH$_2$ in the presence of THF solvent at 80° C. to obtain the desired compound of formula (15). The progress rate of the reduction under condition b-3 as defined above is somewhat low (maximum 25% progress rate). Under reaction condition b-4 as defined above, the best result in terms of the yield can be obtained when the reaction is conducted using 2.0 equivalents of BH$_3$.DMS in toluene solvent at 50° C. (14:15:15a=11.4:61.2:10.7). Among them, a compound of formula (15a) can be debenzylated by hydrogenation in the presence of Pd/C-based catalysts to obtain the compound of formula (4) as defined above.

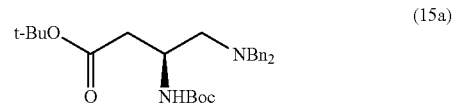

In reaction step (c), the compound of formula (15) can be debenzylated, for example, through debenzylation reaction using H$_2$ and Pd/C for benzyl protecting group or dearylation reaction using PdCl$_2$/1,3-dimethylbarbituric acid to obtain the compound of formula (4).

The third method for preparation of the compound of formula (4) comprises (a) the step of converting the carboxylic acid compound of formula (13) into an activated ester, which is then reacted with a nitrogen source compound to obtain an amide compound of formula (16), (b) the step of reducing an amide group of the amide compound of formula (16) to obtain a nitrile compound of formula (17), and (c) the step of subjecting the nitrile compound of formula (17) to hydrogenation reaction to obtain the compound of formula (4). This method can be represented as shown in the following reaction scheme 8.

Reaction Scheme 8

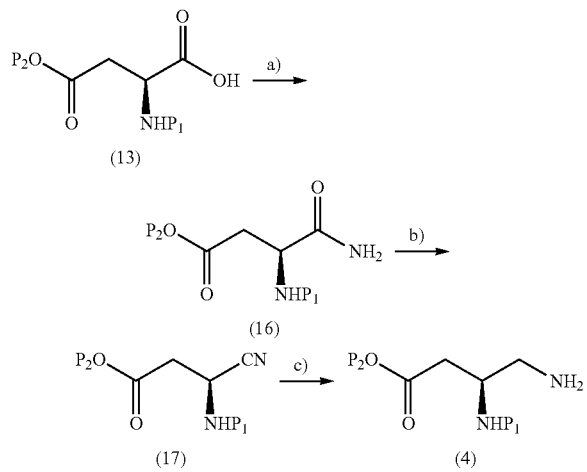

In the above scheme, a is selected from the conditions (1) EtOCOCl, NMM, NH3(g), and (2) Boc$_2$O, NH$_4$HCO$_3$, pyridine, DMF;

b is selected from the conditions (1) (CF$_3$CO)$_2$O, Et$_3$N, and (2) cyanuric acid, DMF;

c is selected from the conditions (1) Pd/C, H$_2$, AcOH, 45 psi, (2) NiCl.6H$_2$O, NaBH$_4$, (3) CF$_3$CO$_2$H, NaBH$_4$, (4) PtO$_2$, H$_2$, AcOH, (5) PtO$_2$, H$_2$, EtOH, CHCl$_3$, (6) Pd(OH)$_2$, H$_2$, MeOH:AcOH (1:1) or AcOH:toluene (1:1), and (7) Pd(OH)$_2$, H$_2$, AcOH; P$_1$ and P$_2$ are as defined above.

Specifically, in step (a) the carboxylic acid group of the starting compound of formula (13) is converted into the activated ester group using chloroformate or Boc$_2$O as an activating agent under the base condition and then reacted with a nitrogen source compound such as ammonia gas or ammonium salt (e.g., ammonium bicarbonate or ammonium carbonate, etc.) to obtain the amide compound of formula (16). In this case, when in the compound of formula (13) P$_1$ is Boc and P$_2$ is i-propyl group or t-butyl group, the result of the reaction is preferable in terms of the yield.

In step (b), the amide group of the compound of formula (16) thus obtained is reacted with trifluoromethane sulfonic acid anhydride/Et$_3$N or cyanuric acid/DMF to obtain the compound of formula (17) having a nitrile group (—CN).

In step (c), hydrogenation can be conducted utilizing a metal selected from palladium, nickel(I) chloride, platinum (IV) oxide or palladium hydroxide to obtain the primary amine compound of formula (4).

The present invention is illustrated in further detail by means of the following Preparations and Examples. However, it is not intended that the scope of the present invention is limited in any manner by these Preparations and Examples.

Advantageous Effects of Invention

The method of the present invention can produce the compound of formula (2) having high optical purity as the intermediate for preparing the compound of formula (1), which can be used as a medicine for treatment or prevention of diseases, including diabetes, caused by the action of dipeptidyl peptidase IV, with high optical purity.

MODE FOR THE INVENTION

Preparation 1

Synthesis of diethyl 2,2-difluoropentanedioate

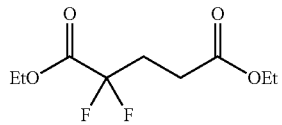 [SMILES: CCOC(=O)CCC(F)(F)C(=O)OCC]

To a solution of ethyl bromodifluoroacetate (33.2 g) in tetrahydrofuran (94.0 g) was added ethyl acrylate (8.2 g) and copper powder (10.9 g). After heating to 50° C., TMEDA (9.5 g) was added dropwise and the reaction mixture was then stirred for 3 hours at the same temperature. Upon disappearance of ethyl acrylate as the starting material, to the reaction solution was added methyl t-butyl ether (MTBE, 73.7 g) followed by addition of 10% aqueous ammonium chloride solution (49.8 g) dropwise, and the mixture was then stirred for 30 minutes. The remaining copper residue was removed by filtration through a celite, and methyl t-butyl ether (MTBE, 66.3 g) was added to separate the layers. The separated organic layer was washed successively with 10% aqueous NH$_4$Cl solution (66.3 g) and 3 N aqueous hydrochloric acid solution (99.6 g) in order and then distilled under reduced pressure to obtain 55.0 g of the desired title compound.

$^1$H NMR (400 MHz, CDCl$_3$) δ 1.26 (t, J=7.2 Hz, 3H), 1.37 (t, J=7.2 Hz, 3H), 2.37-2.49 (m, 2H), 2.55 (t, J=7.2 Hz, 2H), 4.16 (q, J=7.2 Hz, 2H), 4.29 (q, J=7.2 Hz, 2H).

Preparation 2

Synthesis of ethyl 4,4-difluoro-5-hydroxypentanoate

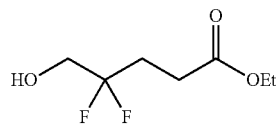 [SMILES: CCOC(=O)CCC(F)(F)CO]

14.8 g of the compound obtained from the above Preparation 1 was diluted with ethanol (20.4 g) and tetrahydrofuran (69.1 g) and then cooled to 0° C. To this solution was slowly added sodium borohydride (NaBH$_4$, 3.5 g) stepwise while keeping the internal temperature below 30° C. After confirming completion of the reaction by $^1$H NMR, the reaction solution was cooled to the temperature of 10° C. and 10% aqueous ammonium chloride solution (77.7 g) was slowly added. The remaining boron compound was filtered through celite, and the filtrate was distilled under reduced pressure to remove tetrahydrofuran. Then, ethyl acetate (105.2 g) was added to separate the layers, and the organic layer was distilled under reduced pressure to obtain 10.8 g of the title compound.

$^1$H NMR (400 MHz, CDCl$_3$) δ 1.23 (t, J=7.2 Hz, 3H), 2.15-2.29 (m, 2H), 2.49 (t, J=7.2 Hz, 2H), 3.69 (t, J=12.0 Hz, 2H), 4.12 (q, J=4.0 Hz, 2H).

Example 1

Synthesis of ethyl 4,4-difluoro-5-{[(trifluoromethyl)sulfonyl]oxy}-pentanoate

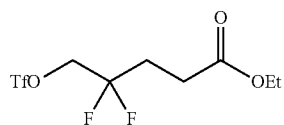 [SMILES: CCOC(=O)CCC(F)(F)COS(=O)(=O)C(F)(F)F]

To the solution of 10.8 g of the compound, as obtained from the above Preparation 2, dissolved in dichloromethane (100.2 g) was added pyridine (7.0 g), and then the mixture was cooled to −5.0° C. After completion of cooling, trifluoromethane sulfonic acid anhydride (20.1 g) was slowly added dropwise while keeping the reaction temperature below 6.3° C. After stirring the reaction solution for 30 minutes, 1.5 N hydrochloric acid solution was added dropwise at 0° C. to separate the layers. The aqueous layer as separated was back-extracted twice with dichloromethane (33.4 g), and the extracts were combined with the organic layer separated from the above and then distilled under reduced pressure to obtain 19.7 g of the title compound as a yellow oil.

$^1$H NMR (500 MHz, CDCl$_3$) δ 1.27 (t, J=7.2 Hz, 3H), 2.29-2.39 (m, 2H), 2.59 (t, J=7.6 Hz, 2H), 4.18 (q, J=7.2 Hz, 2H), 4.55 (t, J=11.6 Hz, 2H).

Example 2-1

Synthesis of ethyl 4,4-difluoro-5-{[(nonafluorobutyl)sulfonyl]-oxy}pentanoate

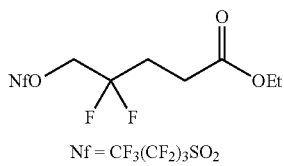

Nf = CF$_3$(CF$_2$)$_3$SO$_2$

To the solution of 100.0 g of the compound, as obtained from the above Preparation 2, dissolved in dichloromethane (300.0 ml) was added pyridine (65.7 g), and the mixture was then cooled to −10.0° C. After completion of cooling, nonafluorobutanesulfonic anhydride (477.4 g) was slowly added dropwise. After stirring the reaction solution for 3 hours, 1.0 N hydrochloric acid solution (300.0 ml) was added dropwise to separate the layers. The aqueous layer as separated was back extracted once with dichloromethane (500.0 ml), and the extracts were combined with the organic layer separated from the above and then distilled under reduced pressure to obtain 177.5 g of the title compound.

$^1$H NMR (500 MHz, CDCl$_3$) δ 1.26 (t, 3H, J=7.3 Hz), 2.30-2.36 (m, 2H), 2.58 (t, 2H, J=7.4 Hz), 4.16 (q, 2H, J=7.3 Hz), 4.57 (t, 2H, J=11 Hz).

Example 2-2

Synthesis of ethyl 4,4-difluoro-5-{[(nonafluorobutyl)sulfonyl]-oxy}pentanoate

To the solution of 500.0 g of the compound, as obtained from the above Preparation 2, dissolved in dichloromethane (1000.0 ml) was added triethylamine (389.0 g), and the mixture was then cooled to 0° C. After completion of cooling, perfluorobutanesulfonyl chloride (948.80 g) was slowly added dropwise. The reaction solution was stirred for 3 hours at room temperature, distilled under reduced pressure, dissolved in methyl t-butyl ether (MTBE, 3000.0 ml) and then washed three times with water. The organic layer thus obtained was dehydrated with magnesium sulfate, filtered through a celite and then distilled under reduced pressure to obtain 960.0 g of the title compound.

Example 3

Synthesis of methyl (2S)-2-[tert-butoxycarbonyl)amino]-4-oxopentanoate

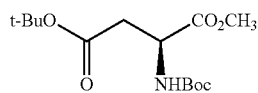 [SMILES: COC(=O)[C@H](CC(=O)OC(C)(C)C)NC(=O)OC(C)(C)C]

To 25.0 g of the starting material, (3S)-3-[(t-butoxycarbonyl)amino]-4-oxopentanoic acid, was added t-butanol (96.9 g) followed by the addition of Boc$_2$O (25.4 g) and dimethylaminopyridine (DMAP, 62.0 g, 0.5 mol %) at room temperature, and the reaction mixture was then stirred for 23 hours at 40° C. Upon completion of the reaction, ethylene dichloride (62.3 g) in t-butanol was added, and the mixture was then distilled under reduced pressure to obtain 30.7 g of the title compound.

$^1$H NMR (400 MHz, CDCl$_3$) δ 1.45 (s, 9H), 1.47 (s, 9H), 2.71 (dd, J=4.8, 16.4 Hz, 1H), 2.88 (dd, J=4.4, 16.4 Hz, 1H), 3.75 (s, 3H), 4.53 (m, 1H), 5.44 (br d, J=8.0 Hz, 1H).

Example 4

Synthesis of tert-butyl (3S)-3-[(tert-butoxycarbonyl)amino]-4-hydroxy-butanoate

30.7 g of the compound obtained from the above Example 3 was dissolved in ethanol (112.3 g) and, after lowering the internal temperature to 10.5° C. sodium borohydride (NaBH$_4$, 5.7 g) was slowly added dropwise. This reaction solution was stirred while maintaining the temperature below 22° C. After confirming completion of the reaction by $^1$H NMR and TLC, to the reaction solution was slowly added 3.0 N hydrochloric acid solution (30.7 g) dropwise at the internal temperature of 10° C. followed by addition of diluted 0.2% hydrochloric acid solution (100.0 g). The reaction solution was adjusted to pH 3~4 with addition of 9.0% aqueous hydrochloric acid solution, and then back-extracted twice with ethyl acetate (100.0 g) and toluene (44.0 g). The organic layer thus obtained was distilled under reduced pressure to obtain 25.1 g of the title compound.

$^1$H NMR (500 MHz, CDCl$_3$) δ 1.44 (s, 9H), 1.45 (s, 9H), 2.48-2.57 (m, 2H), 3.69 (d, J=4.9 Hz, 1H), 3.97 (m, 1H), 5.22 (bs, 1H).

Example 5 tert-butyl (3S)-[(tert-butoxycarbonyl)amino]-4-[(methylsulfonyl)oxy]-butanoate

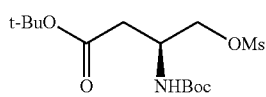

To 25.1 g of the compound obtained from the above Example 4 was added dichloromethane (133.0 g) and triethylamine (148.0 g), and the mixture was then cooled to 0° C. To this reaction solution was slowly added methanesulfonyl chloride (11.8 g) diluted with dichloromethane (39.9 g) dropwise for 50 minutes while maintaining the internal temperature below 12° C. After completion of the reaction, the reaction solution was washed with 0.5 N aqueous hydrochloric acid solution (120.0 g) and water (100.4 g), and then distilled under reduced pressure to obtain 31.5 g of the title compound.

$^1$H NMR (500 MHz, CDCl$_3$) δ 1.44 (s, 9H), 1.46 (s, 9H), 2.62 (d, J=6.0 Hz, 2H), 3.04 (s, 3H), 4.21 (m, 1H), 4.30 (d, J=5.2 Hz, 2H), 5.16 (br d, J=7.2 Hz, 1H).

Example 6

Synthesis of tert-butyl (3S)-4-azido-3-[(tert-butoxycarbonyl)amino]-butanoate

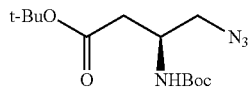 [SMILES: CC(C)(C)OC(=O)C[C@@H](CN=[N+]=[N-])NC(=O)OC(C)(C)C]

Sodium azide (NaN$_3$, 11.6 g) was diluted with dimethylacetamide (DMAc, 260.0 g). After elevating the internal temperature to 80° C., a solution of 31.5 g of the compound, as obtained from the above Example 5, diluted with dimethylacetamide (DMAc, 45.0 g) was added thereto. The reaction proceeded at 80° C. for 2 hours. To the reaction solution were added toluene (251.0 g) and water (320.0 g) to separate the layers. The organic layer thus obtained was distilled under reduced pressure to obtain 24.0 g of the title compound.

$^1$H NMR (500 MHz, CDCl$_3$) δ 1.47 (s, 9H), 1.49 (s, 9H), 2.49 (d, J=6.0 Hz, 2H), 3.44-3.55 (m, 2H), 4.09 (br s, 1H), 5.14 (br s, 1H).

Example 7

Synthesis of tert-butyl (3S)-4-amino-3-[(tert-butoxycarbonyl)amino]-butanoate

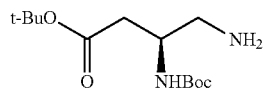 [SMILES: CC(C)(C)OC(=O)C[C@@H](CN)NC(=O)OC(C)(C)C]

To 21.0 g of the compound obtained from the above Example 6 was added tetrahydrofuran (93.3 g) followed by the addition of triphenylphosphine (PPh$_3$, 21.0 g) at 40° C., the mixture was stirred for 2 hours at the same temperature, and water (3.8 g) was then added thereto. The reaction solution was distilled under reduced pressure, and the resulting triphenylphosphine oxide solid was diluted with toluene (26.0 g) and n-hexane (41.0 g), and then filtered off. The filtrate was adjusted to pH 2-3 with 1.0 N aqueous hydrochloric acid solution (110.0 g) and then subjected to separation of the layers. To remove any residual triphenylphosphine oxide solid, the aqueous layer obtained above was washed with dichloromethane (100.0 g) and then adjusted to pH 8-9 with 28% aqueous ammonia solution (7.6 g). The aqueous solution thus obtained was extracted with dichloromethane (100.0 g) and distilled under reduced pressure to obtain 8.5 g of the title compound as a white solid.

$^1$H NMR (500 MHz, CDCl$_3$) δ 1.44 (s, 9H), 1.45 (s, 9H), 2.45 (d, J=6.1 Hz, 2H), 2.77 (d, J=5.5 Hz, 2H), 3.87 (br s, 1H), 5.22 (br s, 1H).

Example 8

Synthesis of N,N-dibenzyl-L-N(Boc)-aspartamide 4-tert-butyl ester

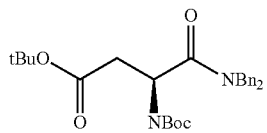

N-Boc-L-aspartic acid 4-t-butyl ester (29.0 g, 0.10 mol) was added to THF (200 ml). After cooling to temperature below −5° C., to the reaction solution was added isobutyl-chloroformate (13.0 ml, 0.10 mol) followed by addition of N-methyl morpholine (12.0 ml, 0.10 mol) dropwise, and the reaction mixture was stirred for over 30 minutes. To the reaction mixture was added dropwise dibenzylamine (21.1 ml, 0.11 mol), and the mixture was then stirred for over 3 hours and monitored for the reaction progress by TLC (EtOAc:Hexane=1:4). Upon completion of the reaction, the reaction solution was stirred with addition of ethyl acetate (300.0 mL) and 1 N hydrochloric acid to separate the layers, and distilled under reduced pressure to precipitate a solid. The solid was filtered and washed with ethyl acetate (100 ml), and then the washings were concentrated by distillation again under reduced pressure. The residue was then subjected to silica gel column to obtain the purified desired product (41.7 g, 0.89 mol).

$^1$H NMR (400 MHz, CDCl$_3$) δ: 7.32 (m, 5H), 7.20 (m, 5H), 5.39 (d, J=7.2 Hz, 1H), 5.30 (m, 1H), 4.87-4.77 (m, 2H), 4.48-4.39 (m, 2H), 2.72 (dd, J=15.8 Hz, J=8.0 Hz, 1H), 2.56 (dd, J=15.8 Hz, J=6.4 Hz, 1H), 1.43 (s, 9H), 1.37 (s, 9H).

Mass (ESI, m/z): 491 (M+Na), 469 (M+H), 413 (M−55).

Example 9

Synthesis of N,N-diallyl-L-N(Boc)-aspartamide 4-tert-butyl ester

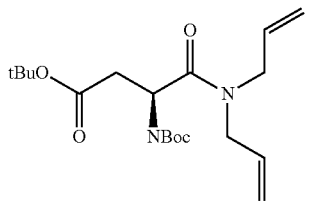

L-N(Boc)-aspartic acid 4-t-butyl ester (5.00 g, 17.3 mol) was added to THF (50 ml). After cooling to temperature below −5° C., to the reaction solution was added isobutylchloroformate (2.26 ml, 17.3 mol) followed by addition of N-methyl morpholine (1.90 ml, 17.3 mol) dropwise, and the reaction mixture was stirred for over 30 minutes. To the reaction mixture was added dropwise diallylamine (2.35 ml, 19.0 mol), and the mixture was then stirred for over 3 hours and monitored for the reaction progress by TLC (EtOAc: Hexane=1:4). Upon completion of the reaction, the reaction solution was stirred with addition of ethyl acetate (60 ml) and 1 N hydrochloric acid and, after separating the layers, concentrated by distillation under reduced pressure. The residue was then subjected to silica gel column to obtain the purified desired product (6.0 g, 16.3 mol).

$^1$H NMR (400 MHz, CDCl$_3$) δ: 5.78 (m, 2H), 5.30 (m, 1H), 5.23-5.11 (m, 1H), 5.30 (m, 1H), 4.93 (m, 1H), 4.11-3.84 (m, 4H), 2.68 (dd, J=15.8 Hz, J=8.0 Hz, 1H), 2.51 (dd, J=15.8 Hz, J=8.0 Hz, 1H), 1.44 (s, 9H), 1.42 (s, 9H).

Mass (ESI, m/z): 391 (M+Na), 369 (M+H), 313 (M−55).

Example 10

Synthesis of N,N-dibenzyl-4-amino-3(S)—N(Boc)-aminobutanoic acid 4-tert-butyl ester

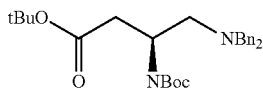

10.0 g of the compound obtained from the above Example 8, Ru$_3$(CO)$_{12}$ (136 mg, 1 mol %), and diphenylsilane (19.7 ml, 106.7 mmol) were added to tetrahydrofuran (50 ml), and the reaction solution was stirred under reflux for over 40 hours. The reaction solution was extracted with ethyl acetate (200 ml) and concentrated by distillation under reduced pressure. The residue was then subjected to silica gel column to obtain the purified desired product (4.7 g, 10.5 mmol).

$^1$H NMR (400 MHz, CDCl$_3$) δ: 7.31-7.20 (m, 10H), 5.12 (bs, 1H), 3.90 (bs, 1H), 3.63 (d, J=12.0 Hz, 2H), 3.48 (d, J=12.0 Hz, 2H), 3.24 (m, 1H), 3.16 (bs, 1H), 2.42 (m, 2H), 1.81 (m, 1H), 1.59 (m, 9H), 1.46 (s, 9H), 1.06 (s, 9H)

Mass (ESI, m/z): 455 (M+H), 441 (M−13). .

Example 11

Synthesis of tert-butyl (3S)-4-amino-3-[(tert-butoxycarbonyl)amino]-4-oxobutanoate

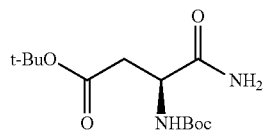 [SMILES: CC(C)(C)OC(=O)C[C@H](NC(=O)OC(C)(C)C)C(N)=O]

360.0 g of the starting material, N-Boc-Asp(O-t-Bu)OH, together with Boc$_2$O (353.0 g) and ammonium bicarbonate (NH$_4$HCO$_3$, 123.9 g) was added to dimethylformamide (1174.6 g), and pyridine (61.0 g) was added dropwise thereto at room temperature, and the reaction mixture was then stirred for about 3 hours. Upon completion of the reaction, water (1440 ml) and toluene (1800 ml) were added to the reaction solution and stirred for 30 minutes to separate the layers. The organic layer thus obtained was distilled under reduced pressure to remove t-butanol and toluene to obtain the title compound, which was directly used in the next reaction.

Example 12

Synthesis of (S)-tert-butyl 3-(tert-butoxycarbonylamino)-3-cyanopropanoate

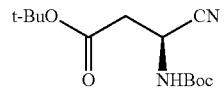

To the compound obtained from Example 11 was added dimethylformamide (1019.5 g) followed by addition of cyanuric chloride (112.0 g) dropwise for 1.5 hours at temperature below 25° C. The reaction solution was stirred for one hour at room temperature, and then 0.1 N aqueous sodium hydroxide solution (1850.0 g) and toluene (1860 ml) were added thereto to separate the layers. The organic layer thus obtained was washed once again with water (700 ml) and then distilled under reduced pressure to obtain 318.3 g of the title compound.

$^1$H NMR (500 MHz, CDCl$_3$) δ: 1.44 (s, 9H), 1.45 (s, 9H), 2.45 (d, J=6.1 Hz, 2H), 2.77 (d, J=5.5 Hz, 2H), 3.87 (br s, 1H), 5.22 (br s, 1H).

Example 13

Synthesis of tert-butyl (3S)-4-amino-3-[(tert-butoxycarbonyl)amino]-butanoate

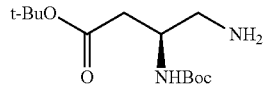

To 212.1 g of the compound obtained from the above Example 12 was added acetic acid (4000 ml) followed by addition of 20 wt % Pd(OH)₂ (1.1 g) at 40° C. The mixture was stirred for 8 hours while keeping the internal temperature below 45° C. and 3 atmospheric pressure of hydrogen. Upon completion of the reaction, the reaction solution was distilled under reduced pressure to remove acetic acid, diluted with toluene (640 L) and then filtered through a celite. To the filtrate was added 0.25 N aqueous hydrochloric acid solution (1060 ml) to separate the layers. The aqueous layer thus obtained was basified with aqueous ammonia solution (543.1 g) and then extracted with methyl t-butyl ether (MTBE, 1000 ml). The organic layer thus obtained was distilled under reduced pressure to obtain 185.0 g of the title compound.

Example 14

Synthesis of 3-t-butoxycarbonylamino-4-(5,5-difluoro-2-oxo-piperidin-1-yl)-butyric acid t-butyl ester

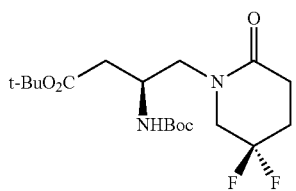

Triethylamine (13.2 g) was added to 16.0 g of the compound obtained from the above Example 1 or 2-1 or 2-2, and 14.1 g of the compound obtained from the above Example 7 or 13, and the mixture was then stirred for 21 hours at 40° C. Then, dichloromethane (154.8 g) and acetic acid (18.3 g) were added, and the mixture was stirred for 5 hours at room temperature. To the resulting reaction solution was added 0.5 N aqueous hydrochloric acid solution (116.8 g) and then, the mixture was stirred for 30 minutes to separate the layers. The organic layer thus obtained was distilled under reduced pressure to obtain 23.6 g of the title compound.

¹H NMR (500 MHz, CDCl₃) δ: 1.42 (s, 9H), 1.46 (s, 9H), 2.27 (m, 2H), 2.40-2.64 (m, 4H), 3.20 (dd, J=4.3, 13.5 Hz, 1H), 3.56-3.70 (m, 2H), 3.76-3.91 (m, 2H), 4.16 (m, 1H), 5.20 (d, J=8.6 Hz, 1H).

Example 15

Synthesis of 3-t-butoxycarbonylamino-4-(5,5-difluoro-2-oxo-piperidin-1-yl)-butyric acid

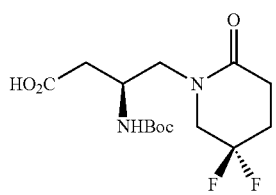

23.6 g of the compound obtained from the above Example 14 was added to dichloromethane (20.0 g) followed by addition of H₃PO₄ (30.0 g), and the mixture was stirred for 16 hours at room temperature. After confirming the detachment of all of t-butyl group and t-butyloxycarbonyl group, the reaction solution was adjusted to pH 7.08.0 with 10 N aqueous sodium hydroxide, and Boc₂O (16.0 g) was added thereto. After completion of the addition, 10 N aqueous sodium hydroxide was used to maintain the pH of the reaction solution at 8.0~9.0. After stirring for 3 hours, the resulting sodium phosphate was filtered off, and the filtrate was then adjusted to pH 2.0~3.0 with 3.0 N aqueous hydrochloric acid solution. The resulting solid was filtered and dried under nitrogen to obtain 14.5 g of the title compound.

¹H NMR (500 MHz, CDCl₃) δ: 1.32 (s, 9H), 2.20-2.43 (m, 6H), 3.26-3.31 (m, 2H), 3.61 (m, 1H), 3.81 (m, 1H), 4.02 (m, 1H), 6.73 (d, J=8.6 Hz, 1H), 12.16 (s, 1H).

For the title compound resulting from the above, its enantiomeric isomers—i.e. S— form and R-form—were measured by HPLC (high-performance liquid chromatography), and an excess of the enantiomeric isomers (S vs. R form) (enantiomeric excess; ee) was then calculated as being ee>99%. On the other hand, in case of the Comparative Example prepared according to the prior method based on WO 06/104356, as described below, the excess (ee) of enantiomeric isomers (S vs. R form) was 80%. From this, it can be identified that the compound of formula (2) having an optically high purity could be obtained according to the method of the present invention.

Comparative Example 1

Synthesis of 3-t-butoxycarbonylamino-4-(5,5-difluoro-2-oxo-piperidin-1-yl)-butyric acid t-butyl ester Comparative Example 1-1

Synthesis of methyl 5-amino-4,4-difluoropentanoate HCl

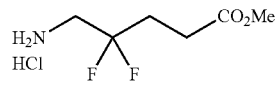

To 10.0 g of the compound obtained from Example 1 was added 40 ml of anhydrous ammonia solution (7 M solution in methanol), and the mixture was stirred for 3 hours. The reaction solution was distilled and 30 ml of hydrochloric acid solution saturated with methanol was added dropwise thereto. The reaction mixture was stirred at room temperature and then distilled to obtain 7.2 g of the title compound as a white solid.

¹H NMR (500 MHz, CD₃OD) δ: 2.35 (m, 2H), 2.59 (t, J=7.6 Hz, 2H), 3.49 (t, J=15.3 Hz, 2H), 3.68 (s, 3H).

Comparative Example 1-2

Synthesis of 3-t-butoxycarbonylamino-4-(5,5-difluoro-2-oxo-piperidin-1-yl)-butyric acid t-butyl ester To the solution of the compound (1.93 g), as obtained from the above Example 4, dissolved in dichloromethane (20.0 g) and H₂O (4.0 g) were added NaBr (0.8 g) and TEMPO (11 mg, 1 mol %). To this reaction solution was slowly added a solution of 5% NaOCl (11.5 g) and NaHCO₃ (1.7 g) dissolved in H₂O (12.0 g) dropwise for about 2 hours while maintaining the temperature below 5° C. Upon completion of dropwise addition, the reaction solution was stirred for 30 minutes to separate the layers. To the organic layer thus obtained was added the compound (1.6 g) obtained from the above Comparative Example 1-1. After stirring for 15 minutes at room temperature, NaBH(OAc)$_3$ (2.23 g) was added to the reaction solution. After stirring for about 19 hours, 10% aqueous NaHCO$_3$ solution (20.0 g) and 0.5 N aqueous hydrochloric acid solution (20.0 g) were added dropwise to the reaction solution to separate the layers. The organic layer thus obtained was dehydrated under anhydrous MgSO$_4$ to obtain 2.0 g (yield 73%) of the same title compound as Example 14, as a yellow solid. For the title compound resulting from the above, its enantiomeric isomers—i.e., S-form and R—form—were measured by HPLC (high-performance liquid chromatography), and an excess (ee) of the enantiomeric isomers (S vs. R form) was then calculated as being ee=80%.

The invention claimed is:

1. A method for preparation of a compound of formula (2) comprising reacting a compound of formula (4) with a compound of formula (5):

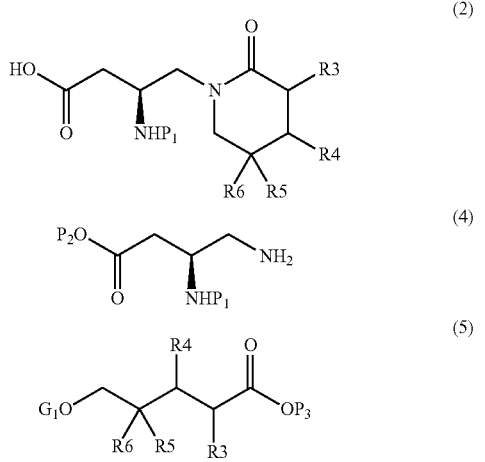

wherein each of R3, R4, R5 and R6 is independently hydrogen, halogen, or substituted or unsubstituted C$_1$-C$_4$ alkyl; P$_1$ is an amine-protecting group; each of P$_2$ and P$_3$ is independently benzyl group, methyl group, ethyl group, i-propyl group or t-butyl group; and G$_1$O is a leaving group.

2. The method according to claim 1, which comprises:
(a) the step of coupling reaction by addition of a base to the compound of formula (4) and the compound of formula (5),
(b) the step of cyclization by addition of an acid to obtain a compound of formula (2a), and
(c) the step of hydrolyzing the resulting compound of formula (2a) to obtain the compound of formula (2):

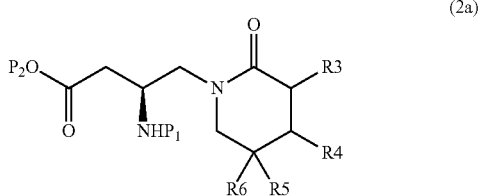

wherein R3, R4, R5, R6, P$_1$ and P$_2$ are as defined in claim 1.

3. The method according to claim 1, wherein P$_2$ is t-butyl group, and P$_3$ is methyl or ethyl group.

4. The method according to claim 1, wherein G$_1$O is triflate, mesylate, tosylate, besylate or nonaflate.

5. The method according to claim 1, wherein R3 and R4 are hydrogen, and R5 and R6 are fluorine.

6. The method according to claim 2, wherein in step (a) C$_1$-C$_4$ trialkylamine is used as the base.

7. The method according to claim 2, wherein in step (b) acetic acid is used as the acid.

8. The method according to claim 2, wherein in the case of the compound of formula (2a) wherein P$_1$ is Boc and P$_2$ is t-butyl, the hydrolysis of said step (c) is conducted under the basic condition to selectively remove only P$_2$ among the protecting groups P$_1$ and P$_2$ to provide the compound of formula (2).

9. The method according to claim 8, wherein aqueous sodium hydroxide solution is used as the base.

10. The method according to claim 1 wherein the compound of formula (5) is prepared by a method comprising:
(a) the step of reducing a compound of formula (7) to obtain a primary alcohol compound; and
(b) the step of reacting the alcohol compound obtained from the above with a G$_1$ compound corresponding to the portion G$_1$O of the compound of formula (5) to obtain the compound of formula (5):

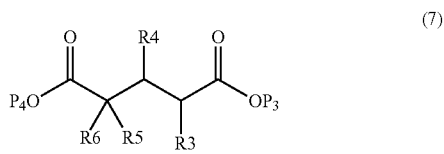

wherein each of R3 and R4 is independently hydrogen or substituted or unsubstituted alkyl;
each of R5 and R6 is independently halogen; and
P$_4$ is benzyl group, methyl group, ethyl group, i-propyl group or t-butyl group.

11. The method according to claim 10, wherein in step (a) the reduction is conducted using NaBH$_4$.

12. The method according to claim 10, wherein in step (b) the G$_1$ compound is selected from the group consisting of trifluoromethane sulfonic acid anhydride (Tf$_2$O), trifluoromethane sulfonyl chloride (TfCl), methanesulfonyl chloride (MsCl), toluenesulfonyl chloride (TsCl), bromobenzenesulfonyl chloride (BsCl), (CF$_3$(CF$_2$)$_3$SO$_2$)F and (CF$_3$(CF$_2$)$_3$ SO$_2$)$_2$O.

13. The method according to claim 1 wherein the compound of formula (4) is prepared by a method comprising:
(a) the step of converting a carboxylic acid of a compound of formula (8) into an ester group by introducing P$_2$ group to obtain a compound of formula (9),
(b) the step of selectively reducing the ester group P$_5$ present in the compound of formula (9) to obtain a compound of formula (10),
(c) the step of introducing G$_2$O leaving group into the compound of formula (10) to obtain a compound of formula (11),
(d) the step of reacting the compound of formula (11) with an azide compound to obtain a compound of formula (12), and
(e) the step of subjecting the compound of formula (12) to hydrogenation to obtain the compound of formula (4):

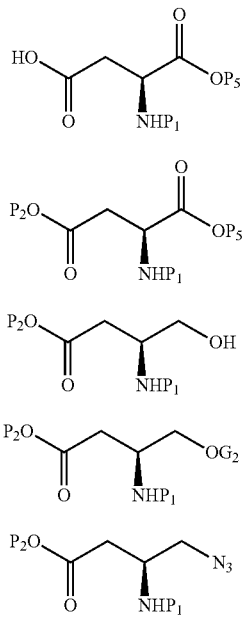

wherein $P_1$ is an amine-protecting group;
$P_2$ is benzyl group, i-propyl group or t-butyl group;
$P_5$ is methyl group, ethyl group, i-propyl group or t-butyl group; and
$G_2O$ is a leaving group;
provided that $P_5$ is methyl group or ethyl group, when $P_2$ is i-propyl group;
$P_5$ is methyl group, ethyl group or i-propyl group, when $P_2$ is t-butyl group; and
$P_5$ is methyl group, ethyl group, i-propyl group or t-butyl group, when $P_2$ is benzyl group.

14. The method according to claim 13, wherein $P_1$ is Boc, $P_2$ is i-propyl group or t-butyl group, and $G_2O$ is triflate or nonaflate.

15. The method according to claim 1 wherein the compound of formula (4) is prepared by a method of comprising:
(a) the step of converting a carboxylic acid compound of formula (13) into an activated ester, which is then reacted with an amine compound to obtain an amide compound of formula (14),
(b) the step of reducing an amide group of the compound of formula (14) to obtain an amine compound of formula (15), and
(c) the step of subjecting the amine compound of formula (15) to debenzylation or deallylation reaction to obtain the compound of formula (4):

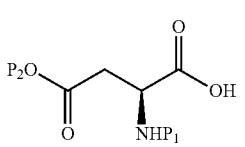

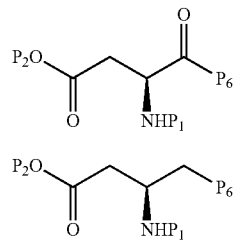

wherein $P_1$ and $P_2$ are as defined in claim 1, $P_6$ is monobenzylamine, dibenzylamine, monoallylamine or diallylamine.

16. The method according to claim 1 wherein the compound of formula (4) is prepared by a method comprising:
(a) the step of converting the carboxylic acid compound of formula (13) into an activated ester, which is then reacted with a nitrogen source compound to obtain an amide compound of formula (16),
(b) the step of dehydrating an amide group of the compound of formula (16) to obtain a nitrile compound of formula (17), and
(c) the step of subjecting the nitrile compound of formula (17) to hydrogenation reaction to obtain the compound of formula (4):

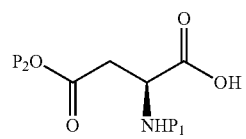

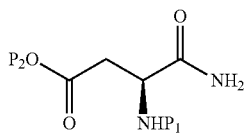

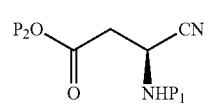

wherein $P_1$ and $P_2$ are as defined in claim 1.

17. The method according to claim 16, wherein $P_1$ is Boc, and $P_2$ is i-propyl or t-butyl.

18. The method according to claim 16, wherein in step (a) chloroformate or $Boc_2O$ is used as the activating agent.

19. The method according to claim 16, wherein the nitrogen source compound used in step (a) is ammonia gas or ammonium salt.

20. The method according to claim 16, wherein in step (b) the dehydration is conducted using trifluoromethane sulfonic acid anhydride and $Et_3N$, or cyanuric chloride and DMF.

21. The method according to claim 16, wherein in step (c) the hydrogenation is conducted using a metal selected from palladium, nickel(I) chloride, platinum(IV) oxide and palladium hydroxide.

22. The method according to claim 16, wherein in step (c) the hydrogenation is conducted using palladium hydroxide metal, acetic acid and hydrogen.

* * * * *